(12) United States Patent
Chen et al.

(10) Patent No.: US 10,604,521 B2
(45) Date of Patent: Mar. 31, 2020

(54) CRYSTALLINE FORMS OF PLX3397 HYDROCHLORIDE, PROCESSES FOR PREPARATION AND USE THEREOF

(71) Applicant: Crystal Pharmaceutical (Suzhou) Co., Ltd., Suzhou, Jiangsu (CN)

(72) Inventors: Minhua Chen, Suzhou (CN); Yanfeng Zhang, Suzhou (CN); Po Zou, Suzhou (CN); Xiaoyu Zhang, Suzhou (CN)

(73) Assignee: Crystal Pharmaceuticals (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/310,163

(22) PCT Filed: Jun. 9, 2017

(86) PCT No.: PCT/CN2017/087711
§ 371 (c)(1),
(2) Date: Dec. 14, 2018

(87) PCT Pub. No.: WO2017/215521
PCT Pub. Date: Dec. 21, 2017

(65) Prior Publication Data
US 2019/0256510 A1   Aug. 22, 2019

(30) Foreign Application Priority Data
Jun. 17, 2016 (CN) .......................... 2016 1 0430773

(51) Int. Cl.
C07D 471/04 (2006.01)
A61P 35/00 (2006.01)
A61K 31/444 (2006.01)

(52) U.S. Cl.
CPC .......... *C07D 471/04* (2013.01); *A61K 31/444* (2013.01); *A61P 35/00* (2018.01); *C07B 2200/13* (2013.01)

(58) Field of Classification Search
CPC .................................................. C07D 471/04
USPC ......................................... 546/113; 514/300
See application file for complete search history.

(56) References Cited

U.S. PATENT DOCUMENTS 6,627,646 B2 * 9/2003 Bakale ................. C07D 401/12
514/303
9,802,932 B2 * 10/2017 Ibrahim ............... A61K 31/444

FOREIGN PATENT DOCUMENTS

CN   101605787 A   12/2009
CN   103497188 A   1/2014
WO   2016/179412 A1   11/2016

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1-33.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*

* cited by examiner

*Primary Examiner* — Patricia L Morris
(74) *Attorney, Agent, or Firm* — McCarter & English, LLP; Steven G. Davis; Wei Song

(57) ABSTRACT

The present disclosure relates to novel crystalline forms of PLX3397 hydrochloride and processes for preparation thereof. The crystalline forms of PLX3397 hydrochloride provided by the present disclosure have higher solubility, larger particle size which is favorable for separation in the subsequent production process, and good stability, especially mechanical stability. These novel crystalline forms of PLX3397 hydrochloride provide a better choice for PLX3397 drug products and are of great value for drug development.

(I)

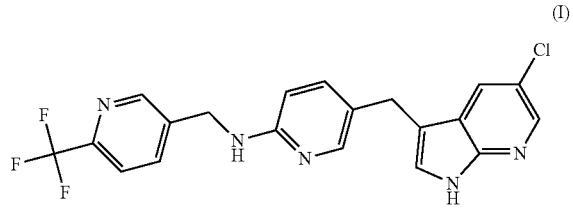

6 Claims, 9 Drawing Sheets

CRYSTALLINE FORMS OF PLX3397 HYDROCHLORIDE, PROCESSES FOR PREPARATION AND USE THEREOF

CROSS-REFERENCE TO RELATED APPLICATIONS

The present application is a U.S. national stage application, filed under 35 U.S.C. § 371(c), of International Application No. PCT/CN2017/087711, filed on Jun. 9, 2017, which claims the priority of Chinese Application No. 201610430773.2, filed on Jun. 17, 2016. The entire contents of the aforementioned applications are incorporated herein by reference.

TECHNICAL FIELD

The present disclosure relates to the field of pharmaceutical crystal technology, particularly relates to novel crystalline forms of PLX3397 hydrochloride, processes for preparation and use thereof.

BACKGROUND

Pexidartinib (PLX3397) is a new drug for the treatment of tenosynovial giant cell tumor (TGCT). TGCT is a rare tenosynovial tumor. Surgery is the primary treatment for TGCT at present, which may lead to deterioration of dysfunction and serious complications. In addition, as TGCT has multiple types, which generally occur at bone tissue and joints, the emergence of new interventional therapies is urgently needed in the clinically. At present, PLX3397 is in phase III clinical trials and has been granted the breakthrough therapy designation from the US Food and Drug Administration (FDA). The structure of PLX3397 is shown as formula (I).

Formula (I)

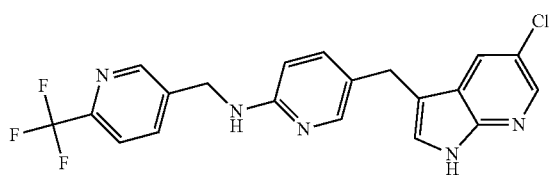

Polymorph or polymorphism is the property of some molecules or molecular complexes. Polymorphism may result from different molecular packing. Polymorphs of a given compound may have different crystal structures and physical properties, such as solubility, stability, thermal property, mechanical property, purification ability, X-ray powder diffraction, infrared spectroscopy, Raman spectroscopy, and solid-state NMR spectroscopy, etc. One or combination of multiple characterization methods may be used to differentiate different crystalline forms of the same molecule or molecular complexes.

Novel crystalline forms (including anhydrates, hydrates and solvates, etc.) of the active pharmaceutical ingredients may offer better processing and physicochemical properties, such as bioavailability, stability, processability, and purification ability. Some novel crystalline forms may serve as intermediate crystal forms to facilitate solid state transformation to desired forms. Novel crystalline forms of a pharmaceutical compound may improve properties of drug product. Novel polymorphs of raw materials provide more solid forms in the formulation, and this can improve dissolution, improve shelf life, and make it easier to process, etc.

Different crystalline forms of solid chemical drugs, which may have different solubility and stability, can affect the absorption and bioavailability of drugs, and lead to differences in clinical efficacy. The clinical form of PLX3397 is monohydrochloride. WO2016179415 first disclosed the crystalline forms of PLX3397 monohydrochloride, including Form A, Form B, Form C and Form D. Form A converted to Form C after stored at 80° C. for 7 days. Form B is not a crystalline form in which Form C is mixed. Form D is a methanol solvate. Form A, B and D are not suitable for drug products development. Form C is the only crystalline form suitable for drug development.

Therefore, it is necessary to carry out a comprehensive systematic polymorph screening of PLX3397, and select more crystalline forms with beneficial properties for drug product development.

The inventors of the present disclosure surprisingly discovered a novel crystalline form of PLX3397 monohydrochloride and a novel crystalline form of PLX3397 dihydrochloride during the research process. The crystalline forms of PLX3397 hydrochloride provided by the present disclosure have higher solubility, larger particle size, which is beneficial to separation in the subsequent production process, and good stability, especially superior mechanical stability compared to that of prior art crystal forms. These novel crystalline forms provide a better choice for PLX3397 drug products and are of great value for drug development.

SUMMARY

In order to overcome the disadvantages of prior art, the main objective of the present disclosure is to provide novel crystalline forms of PLX3397 hydrochloride, processes for preparation and use thereof.

Formula (I)

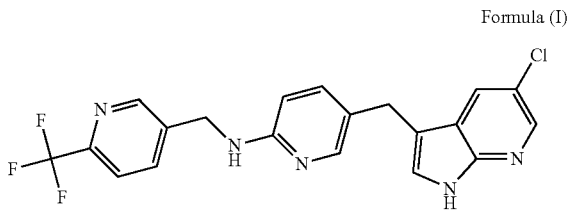 [SMILES: FC(F)(F)c1ccc(CNc2ccc(Cc3c[nH]c4ncc(Cl)cc34)cn2)cn1]

According to the objective of the present disclosure, crystalline form CS2 of PLX3397 monohydrochloride and crystalline form CS3 of PLX3397 dihydrochloride are provided.

One objective of the present disclosure is to provide a crystalline form of PLX3397 monohydrochloride, designated as monohydrochloride Form CS2.

According to one aspect of the present disclosure, the X-ray powder diffraction pattern of monohydrochloride Form CS2 shows characteristic peaks at 2theta values of 7.2°±0.2°, 10.6°±0.2°, 29.3°±0.2° using Cu-Kα radiation.

Furthermore, the X-ray powder diffraction pattern of monohydrochloride Form CS2 shows 1 or 2 diffraction peaks at 2theta values of 14.5°±0.2° and 21.4°±0.2°. Preferably, the X-ray diffraction pattern of monohydrochloride Form CS2 shows diffraction peaks at 2theta values of 14.5°±0.2° and 21.4°±0.2°.

Furthermore, the X-ray powder diffraction pattern of monohydrochloride Form CS2 shows 1 or 2 diffraction peaks at 2theta values of 23.9°±0.2° and 26.9°±0.2°. Preferably, the X-ray diffraction pattern of monohydrochloride Form CS2 shows diffraction peaks at 2theta values of 23.9°±0.2° and 26.9°±0.2°.

In a preferred embodiment, the X-ray powder diffraction pattern of monohydrochloride Form CS2 shows characteristic peaks at 2theta values of 7.2°±0.2°, 10.6°±0.2°, 29.3°±0.2°, 14.5°±0.2°, 21.4°±0.2°, 23.9°±0.2° and 26.9°±0.2°.

In a preferred embodiment, the X-ray powder diffraction pattern of monohydrochloride Form CS2 is substantially as depicted in FIG. 1.

Monohydrochloride Form CS2 is provided in the present disclosure and monohydrochloride Form CS2 is a hydrate.

The $^1$H NMR spectrum of monohydrochloride Form CS2 of the present disclosure is substantially as depicted in FIG. 4. The corresponding data are: $^1$H NMR (400 MHz, DMSO) δ 11.76 (s, 1H), 8.79 (s, 1H), 8.18 (d, J=2.3 Hz, 1H), 8.13-8.01 (m, 2H), 7.99-7.88 (m, 2H), 7.79 (s, 1H), 7.47 (s, 1H), 6.98 (s, 1H), 4.73 (s, 2H), 3.94 (s, 2H).

According to the objective of the present disclosure, a process for preparing monohydrochloride Form CS2 is also provided. The process comprises: adding the solid of PLX3397 into a solvent of alkanes, adding dilute hydrochloric acid solution under stirring, reacting for 0.1-24 hours at 0-25° C., filtering and drying to obtain an off-white solid.

Furthermore, said alkane is n-heptane; the molar ratio of HCl/PLX3397 is 1:1; said reaction temperature is 5° C.; said reaction time is 0.5 hour, and the concentration of said dilute hydrochloric acid solution is 0.2-2 mol/L, preferably 0.6 mol/L.

Another objective of the present disclosure is to provide a novel crystalline form of PLX3397 dihydrochloride, designated as dihydrochloride Form CS3.

The X-ray powder diffraction pattern of dihydrochloride Form CS3 shows characteristic peaks at 2theta values of 17.5°±0.2°, 23.2°±0.2° and 26.4°±0.2° using Cu-Kα radiation.

Furthermore, the X-ray powder diffraction pattern of dihydrochloride Form CS3 shows 1 or 2 or 3 diffraction peaks at 2theta values of 12.7°±0.2°, 14.7°±0.2° and 27.4°±0.2°. Preferably, the X-ray diffraction pattern of dihydrochloride Form CS3 shows diffraction peaks at 2theta values of 12.7°±0.2°, 14.7°±0.2° and 27.4°±0.2°.

Furthermore, the X-ray powder diffraction pattern of dihydrochloride Form CS3 shows 1 or 2 diffraction peaks at 2theta values of 16.5°±0.2°, 22.6°±0.2° and 23.8°±0.2°. Preferably, the X-ray diffraction pattern of dihydrochloride Form CS3 shows diffraction peaks at 2theta values of 16.5°±0.2°, 22.6°±0.2° and 23.8°±0.2°.

In a preferred embodiment, the X-ray powder diffraction pattern of dihydrochloride Form CS3 shows characteristic peaks at 2theta value of 17.5°±0.2°, 23.2°±0.2°, 26.4°±0.2°, 12.7°±0.2°, 14.7°±0.2°, 27.4°±0.2°, 16.5°±0.2°, 22.6°±0.2° and 23.8°±0.2°.

In a preferred embodiment, the X-ray powder diffraction pattern of dihydrochloride Form CS3 is substantially as depicted in FIG. 5.

Dihydrochloride Form CS3 is provided in present disclosure and dihydrochloride Form CS3 is a hydrate.

The $^1$H NMR spectrum of dihydrochloride Form CS3 of the present disclosure is substantially as depicted in FIG. 8. The corresponding data are: $^1$H NMR (400 MHz, DMSO) δ 11.78 (s, 1H), 9.12 (s, 1H), 8.81 (s, 1H), 8.18 (d, J=2.3 Hz, 1H), 8.10 (dd, J=14.8, 5.3 Hz, 2H), 7.99-7.85 (m, 3H), 7.48 (d, J=2.4 Hz, 1H), 7.06 (d, J=9.2 Hz, 1H), 4.78 (s, 2H), 3.96 (s, 2H).

According to the objective of the present disclosure, a process for preparing dihydrochloride Form CS3 is also provided. The process comprises: adding the solid of PLX3397 into an alkane, adding concentrated hydrochloric acid solution under stirring, reacting for 1-16 hours at 0-25° C., filtering and drying to obtain an off-white solid.

Furthermore, said alkane is n-octane; the molar ratio of HCl/PLX3397 is 2:1; said reaction temperature is 5° C.; said reaction time is 2 hours.

Said "concentrated hydrochloric acid" is about 37% hydrochloric acid solution.

In the present disclosure, "crystal" or "crystalline form" refers to the crystal or the crystal form being identified by the X-ray diffraction pattern shown herein. Those skilled in the art are able to understand that physicochemical properties discussed herein can be characterized, wherein the experimental errors depend on the conditions of instruments, the sampling processes and the purity of samples. In particular, those skilled in the art generally know that the X-ray diffraction pattern typically vary with the experimental conditions. It is necessary to point out that, the relative intensity of the diffraction peaks in the X-ray diffraction pattern may also vary with the experimental conditions; therefore, the order of the diffraction peak intensities cannot be the sole or decisive factor. In fact, the relative intensity of the diffraction peaks in the X-ray powder diffraction pattern is related to the preferred orientation of the crystals, and the diffraction peak intensities shown herein are illustrative and not for absolute comparison. In addition, the experimental error of the diffraction peak angle is usually 5% or less, and the error of these angles should also be taken into account, and an error of ±0.2° is usually allowed. In addition, due to experimental factors such as sample thickness, the overall offset of the diffraction peak is caused, and a certain offset is usually allowed. Thus, it will be understood by those skilled in the art that it is unnecessary that the X-ray diffraction pattern of a crystalline form of the present disclosure should be exactly the same with X-ray diffraction patterns of the example shown herein. The "X-ray powder diffraction pattern is the same" as used herein does not mean absolutely the same, the same peak position may differ by ±0.2° and the diffraction peak intensity allows for a certain variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

"Crystalline Form" and "Polymorphic Form" as well as other related terms in the present disclosure refer to the solid compounds whose crystal structure is being in a special crystal form state. The difference in the physical and chemical properties of the polymorphic forms may be embodied in storage stability, compressibility, density, dissolution rate, etc. In extreme cases, the difference in solubility or dissolution rate may result in inefficient drugs, even developing toxicities.

In some embodiments, the novel crystalline forms of the present disclosure, including monohydrochloride Form CS2 and dihydrochloride Form CS3, are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the numerical value and the scope of the present disclosure should not be narrowly understood as a value or numerical value range. It should be understood by those skilled in the art that the specific numerical value can be floated according to the specific technical environment on the basis that the spirit and principle of the disclosure are not depart from the spirit and principle of the disclosure. In the present disclosure, the number of floating ranges which can be expected by one of skilled in the art is represented by the term "about".

According to the objective of the present disclosure, a pharmaceutical composition is provided; said pharmaceutical composition comprises a therapeutically effective amount of monohydrochloride Form CS2, dihydrochloride Form CS3 or combinations thereof, and pharmaceutically acceptable excipients. The pharmaceutical composition or drug product is generally prepared by mixing or combining therapeutically effective amount of monohydrochloride Form CS2, dihydrochloride Form CS3 or combinations thereof with one or more pharmaceutically acceptable excipients. The pharmaceutical compositions are prepared according to known methods in this field.

Monohydrochloride Form CS2 and dihydrochloride Form CS3 of the present disclosure have advantageous properties suitable for the above dosage forms.

Furthermore, monohydrochloride Form CS2 and dihydrochloride Form CS3 or combinations thereof can be used for preparing drugs treating tumor, especially tenosynovial giant cell tumor.

Monohydrochloride Form CS2 and dihydrochloride Form CS3 of PLX3397 provided by the present disclosure have higher solubility, larger particle sizes, which is beneficial to separation in the subsequent production process, and good stability, especially superior mechanical stability compared to that of prior art crystal forms. These novel crystalline forms provide a better choice for the preparation of pharmaceutical preparations containing PLX3397 and are of great value for drug development.

DETAILED DESCRIPTION OF THE DISCLOSURE

Figure 1:
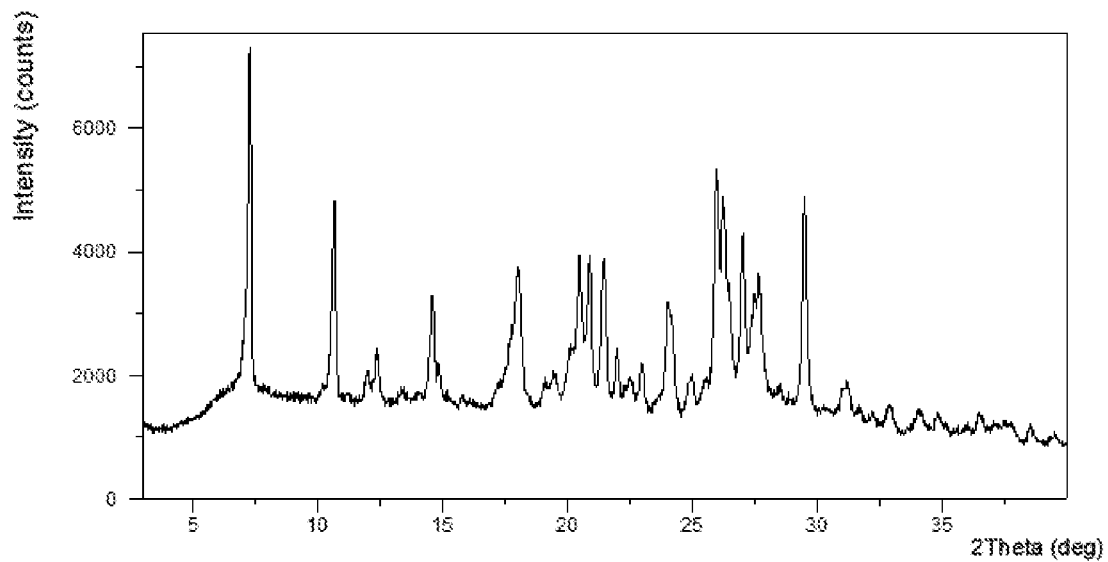
FIG. 1 shows an XRPD pattern of Form CS2 in example 1.

The present disclosure is further illustrated by the following examples which describe the preparation and use of the crystalline forms of the disclosure in detail. It is obvious to those skilled in the art that many changes in the materials and methods can be accomplished without departing from the scope of the disclosure.

The abbreviations used in the present disclosure are explained as follows:
XRPD: X-ray Powder Diffraction
DSC: Differential Scanning Calorimetry
TGA: Thermal Gravimetric Analysis
DVS: Dynamic Vapor Sorption
$^1$H NMR: Proton Nuclear Magnetic Resonance
PSD: Particle Size Distribution
Instruments and methods used to collect data:
X-ray powder diffraction pattern in the present disclosure was acquired by a PANalytical Empyrean X-ray powder diffractometer. The parameters of the X-ray powder diffraction method of the present disclosure were as follows:
X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree
Differential scanning calorimetry (DSC) data in the present disclosure were acquired by a TA Q2000. The parameters of the differential scanning calorimetry (DSC) method of the present disclosure were as follows:
Heating rate: 10° C./min
Purge gas: nitrogen
Thermal gravimetric analysis (TGA) data in the present disclosure are acquired by a TA Q5000. The parameters of the thermal gravimetric analysis (TGA) method of the present disclosure were as follow:
Heating rate: 10° C./min
Purge gas: nitrogen
Proton nuclear magnetic resonance spectrum data (1H NMR) is collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.
Dynamic Vapor Sorption (DVS) is measured via a SMS (Surface Measurement Systems Ltd.) intrinsic DVS. Typical Parameters for DVS test are as follows:

Temperature: 25° C.
Gas and flow rate: $N_2$, 200 mL/min
dm/dt: 0.002%/min
RH range: 0% RH to 95% RH The particle size distribution test in the present disclosure is acquired by the S3500 laser particle size analyzer of Microtrac. Microtrac S3500 is equipped with the SDC (Sample Delivery Controller). The test is carried out by wet process, and the dispersion medium is Isopar G The parameters are as follow:

| | |
|---|---|
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 30 s |

*Flow rate 60% is 60% of 65 mL/s.

The abbreviations used in the present disclosure are explained as follows:

Mv: Average particle size calculated by volume.

D10: particle size which accounts for 10% of the particle size distribution (volume distribution).

D50: particle size which accounts for 50% of the particle size distribution (volume distribution), also known as the median particle size.

D90: particle size which accounts for 90% of the particle size distribution (volume distribution).

High Performance Liquid Chromatography (HPLC) data in the present disclosure are collected from Agilent 1100 with diode array detector (DAD). The HPLC method parameters for solubility test in the present disclosure are as follows:

| | |
|---|---|
| 1. | Column: Waters Xbridge C18 150 × 4.6 mm, 5 μm |
| 2. | Mobile Phase: A: 0.1% TFA in $H_2O$ |
| | B: 0.1% TFA in Acetonitrile |

Gradient:

| Time (min) | % B |
|---|---|
| 0.0 | 20 |
| 25.0 | 80 |
| 30.0 | 80 |
| 30.1 | 20 |
| 35.0 | 20 |

3. Flow rate: 1.0 mL/min
4. Injection Volume: 4 μL
5. Detection wavelength: 230 nm
6. Column Temperature: 40° C.
7. Diluent: 50% Acetonitrile Unless otherwise specified, the following examples were conducted at room temperature.

Raw materials of PLX3397 used in the following examples are prepared by known methods in the prior art.

Example 1 Preparation of Monohydrochloride Form CS2

101.6 mg of PLX3397 freebase was weighed into a 5-mL glass vial followed by adding 2 mL of n-heptane at 5° C. Then, 440 μL of 0.6 mol/L dilute hydrochloride acid solution was added under magnetic stirring. After reacting for 40 minutes, the suspension was filtered and dried, giving an off-white solid.

Figure 4:
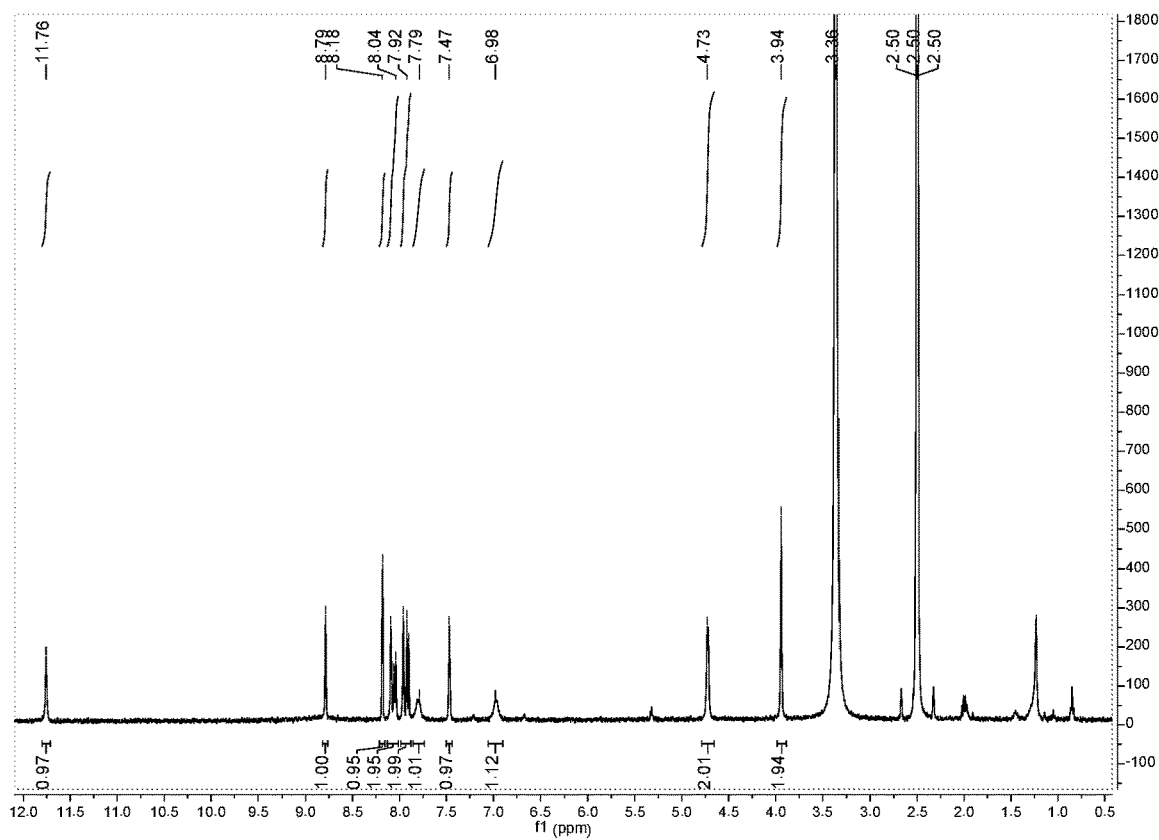
FIG. 4 shows a $^1$H NMR spectrum of Form CS2 in example 1.

The obtained solid conformed to monohydrochloride Form CS2 by XRPD, of which the XRPD pattern was substantially as depicted in FIG. 1, and the XRPD data were listed in Table 1. The obtained solid conformed to PLX3397 monohydrochloride by ion chromatography. The $^1$H NMR spectrum was substantially as depicted in FIG. 4.

Figure 2:
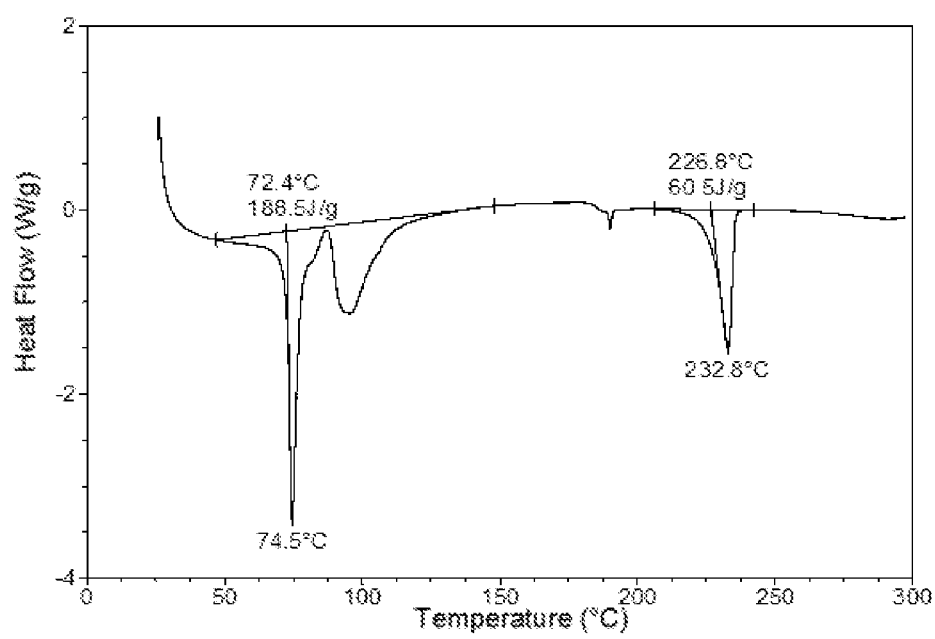
FIG. 2 shows a DSC curve of Form CS2 in example 1.

The DSC curve of Form CS2 was substantially as depicted in FIG. 2. An endothermic peak appeared at around 72° C., and another endothermic peak appeared at around 227° C.

Figure 3:
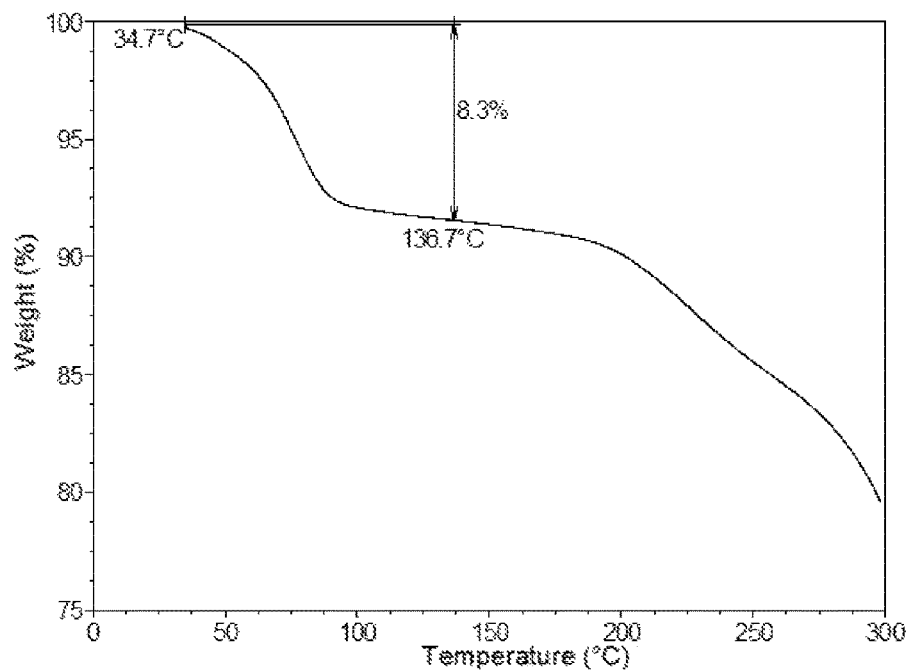
FIG. 3 shows a TGA curve of Form CS2 in example 1.

The TGA curve of Form CS2 showed about 8.3% weight loss when heated to 137° C., which was substantially as depicted in FIG. 3. Without any limitation being implied, Form CS2 is a hydrate.

TABLE 1

| 2θ | d spacing | Intensity % |
|---|---|---|
| 7.20 | 12.28 | 100.00 |
| 10.58 | 8.36 | 57.59 |
| 11.89 | 7.44 | 8.12 |
| 12.31 | 7.19 | 13.73 |
| 13.25 | 6.68 | 2.78 |
| 14.51 | 6.11 | 31.39 |
| 14.75 | 6.00 | 10.37 |
| 17.93 | 4.95 | 41.39 |
| 18.99 | 4.67 | 7.97 |
| 19.36 | 4.59 | 10.75 |
| 19.92 | 4.46 | 14.81 |
| 20.39 | 4.36 | 45.80 |
| 20.80 | 4.27 | 45.33 |
| 21.38 | 4.16 | 42.55 |
| 21.87 | 4.06 | 17.86 |
| 22.39 | 3.97 | 10.95 |
| 22.87 | 3.89 | 14.94 |
| 23.88 | 3.73 | 32.40 |
| 24.09 | 3.69 | 27.25 |
| 24.88 | 3.58 | 12.57 |
| 25.84 | 3.45 | 72.96 |
| 26.10 | 3.41 | 64.60 |
| 26.90 | 3.31 | 55.75 |
| 27.34 | 3.26 | 36.88 |
| 27.54 | 3.24 | 44.09 |
| 29.36 | 3.04 | 67.63 |
| 31.11 | 2.88 | 13.08 |
| 32.08 | 2.79 | 5.23 |
| 32.75 | 2.73 | 7.89 |
| 33.91 | 2.64 | 6.80 |
| 34.72 | 2.58 | 5.51 |
| 36.33 | 2.47 | 7.31 |
| 37.69 | 2.39 | 4.24 |
| 38.39 | 2.34 | 4.25 |

Example 2 Preparation of Dihydrochloride Form CS3

101.5 mg of PLX3397 freebase was weighed into a 5-mL glass vial followed by adding 2.5 mL of n-octane at 5° C. Then, 40 μL of 37% concentrated hydrochloric acid solution was added under magnetic stirring. After reacting for 2 hours, the suspension was filtered and dried, giving an off-whited solid.

Figure 5:
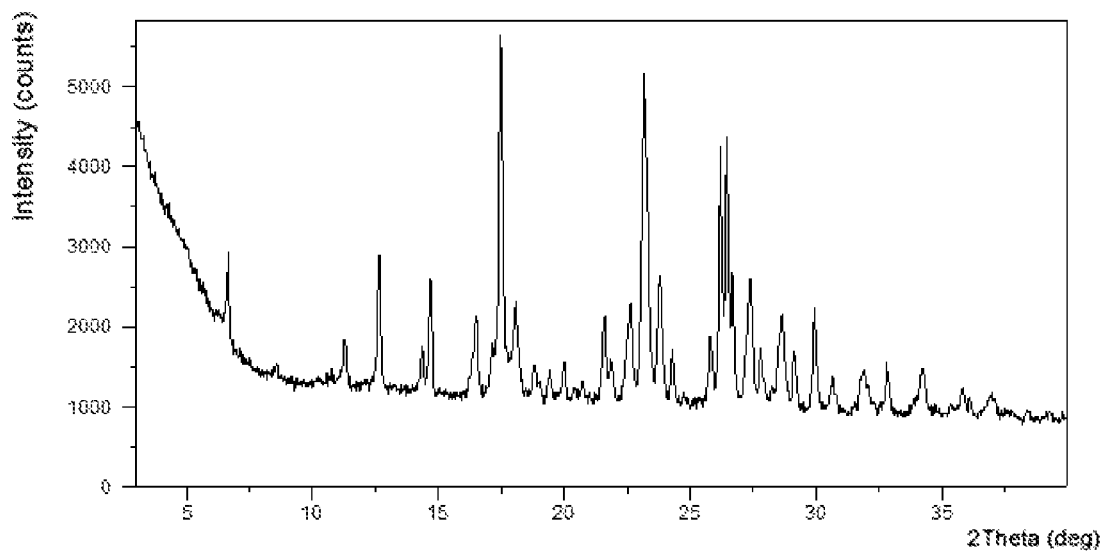
FIG. 5 shows an XRPD pattern of Form CS3 in example 2.

The obtained solid conformed to dihydrochloride Form CS3 by XRPD, of which the XRPD pattern was substantially as depicted in FIG. 5, and the XRPD data were listed in Table 2. The obtained solid conformed to PLX3397 dihydrochloride by ion chromatography.

TABLE 2

| 2θ | d spacing | Intensity % |
|---|---|---|
| 6.65 | 13.29 | 22.22 |
| 11.30 | 7.83 | 12.88 |
| 12.65 | 7.00 | 38.13 |
| 14.35 | 6.17 | 12.51 |
| 14.69 | 6.03 | 31.97 |
| 16.49 | 5.38 | 22.47 |
| 17.48 | 5.07 | 100.00 |
| 18.07 | 4.91 | 24.76 |
| 18.83 | 4.71 | 9.01 |
| 19.43 | 4.57 | 5.87 |
| 19.99 | 4.44 | 10.20 |
| 20.61 | 4.31 | 2.11 |
| 21.58 | 4.12 | 24.36 |
| 21.86 | 4.07 | 11.61 |
| 22.63 | 3.93 | 27.61 |
| 23.16 | 3.84 | 94.09 |
| 23.78 | 3.74 | 36.55 |
| 24.30 | 3.66 | 15.46 |
| 25.82 | 3.45 | 19.70 |
| 26.20 | 3.40 | 73.31 |
| 26.45 | 3.37 | 76.60 |
| 26.70 | 3.34 | 37.00 |
| 27.40 | 3.26 | 36.49 |
| 27.80 | 3.21 | 15.67 |
| 28.69 | 3.11 | 26.33 |
| 29.14 | 3.06 | 16.63 |
| 29.94 | 2.98 | 28.46 |
| 30.67 | 2.92 | 8.72 |
| 31.83 | 2.81 | 10.59 |
| 32.82 | 2.73 | 12.55 |
| 34.22 | 2.62 | 12.41 |
| 35.80 | 2.51 | 7.59 |
| 36.92 | 2.43 | 5.83 |

Example 3 Preparation of Dihydrochloride Form CS3

10.0 mg of PLX3397 freebase was weighed into a 1.5-mL glass vial followed by adding 0.5 mL of n-octane at 5° C. Then, 4 μL of 37% concentrated hydrochloric acid solution was added under magnetic stirring. After reacting for 16 hours, the suspension was filtered and dried, giving an off-whited solid.

Figure 6:
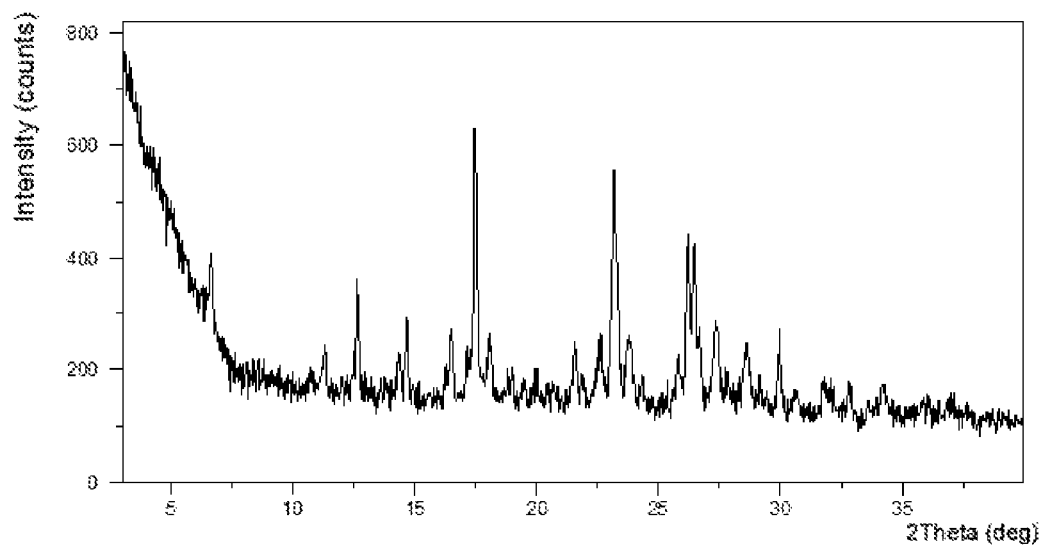
FIG. 6 shows an XRPD pattern of Form CS3 in example 3.
Figure 9:
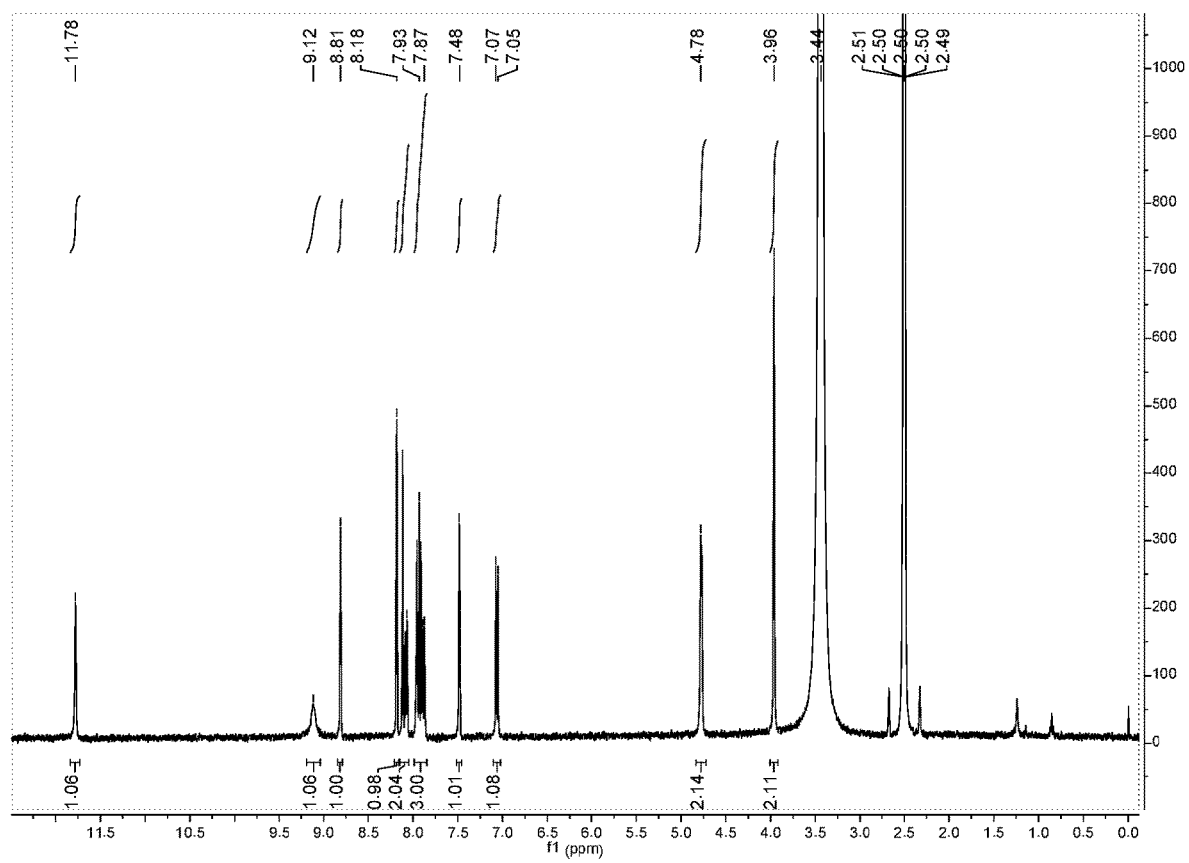
FIG. 9 shows a $^1$H NMR spectrum of Form CS3 in example 3.

The obtained solid conformed to dihydrochloride Form CS3 by XRPD, of which the XRPD pattern was substantially as depicted in FIG. 6, and the XRPD data were listed in Table 3. The $^1$H NMR spectrum was substantially as depicted in FIG. 9.

Figure 7:
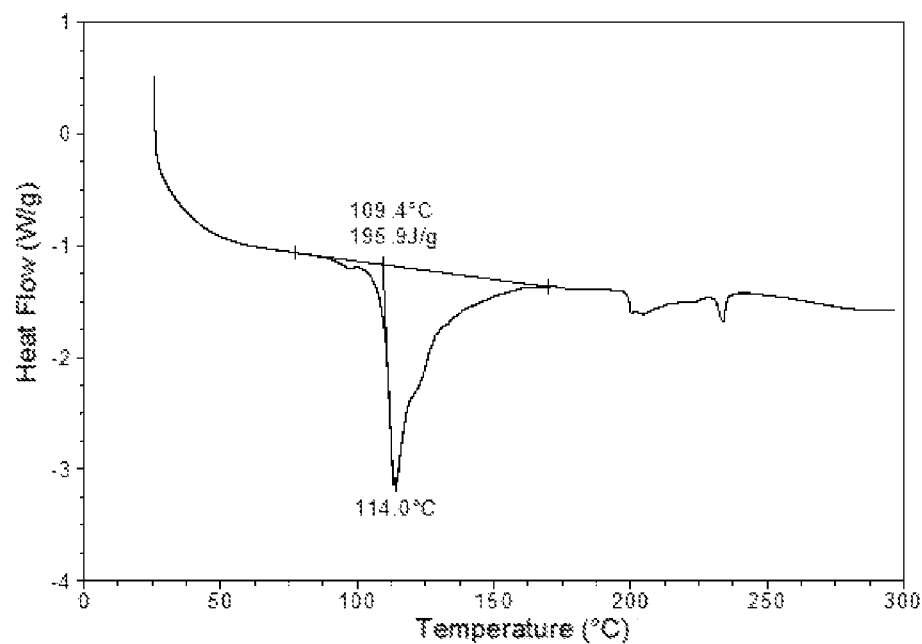
FIG. 7 shows a DSC curve of Form CS3 in example 3.

The DSC curve of Form CS3 was substantially as depicted in FIG. 7. An endothermic peak appeared at around 109° C.

Figure 8:
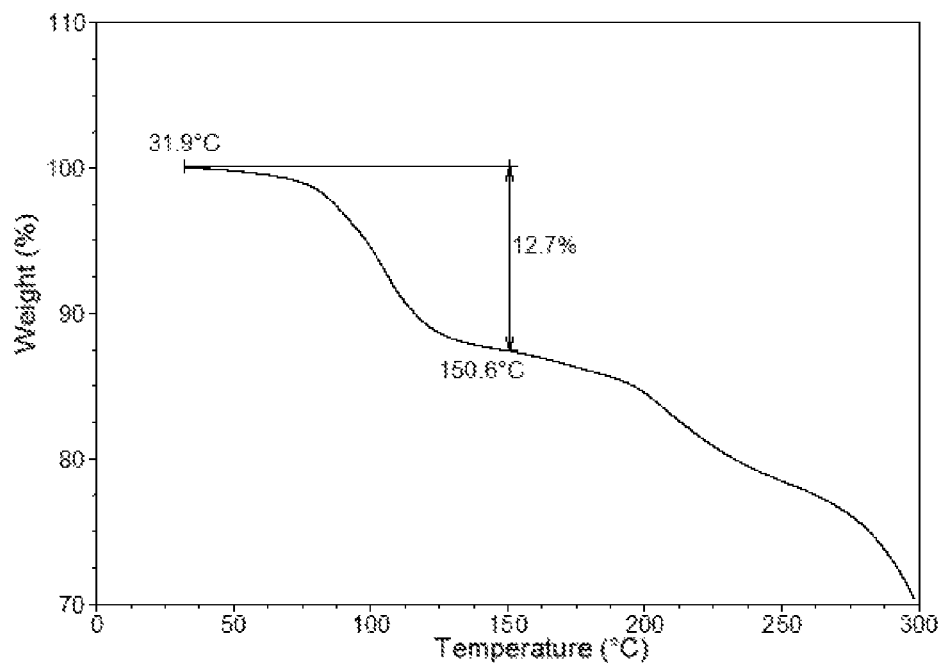
FIG. 8 shows a TGA curve of Form CS3 in example 3.

The TGA curve of Form CS3 showed about 12.7% weight loss when heated to 151° C., which was substantially as depicted in FIG. 8. Without any limitation being implied, Form CS3 is a hydrate.

TABLE 3

| 2θ | d spacing | Intensity % |
|---|---|---|
| 6.63 | 13.32 | 24.86 |
| 11.28 | 7.84 | 15.89 |
| 12.66 | 6.99 | 37.61 |
| 14.69 | 6.03 | 29.18 |
| 16.49 | 5.37 | 25.69 |
| 17.48 | 5.07 | 100.00 |
| 18.08 | 4.91 | 19.59 |
| 21.58 | 4.12 | 21.49 |
| 22.62 | 3.93 | 23.20 |
| 23.16 | 3.84 | 87.45 |

TABLE 3-continued

| 2θ | d spacing | Intensity % |
|---|---|---|
| 23.79 | 3.74 | 25.10 |
| 25.82 | 3.45 | 17.53 |
| 26.19 | 3.40 | 61.10 |
| 26.46 | 3.37 | 64.17 |
| 27.39 | 3.26 | 30.93 |
| 28.60 | 3.12 | 22.49 |
| 29.97 | 2.98 | 29.03 |
| 30.62 | 2.92 | 7.01 |
| 31.83 | 2.81 | 10.57 |
| 32.84 | 2.73 | 9.17 |
| 34.22 | 2.62 | 10.86 |

Example 4 Hygroscopicity Test of Monohydrochloride Form CS2

Figure 10:
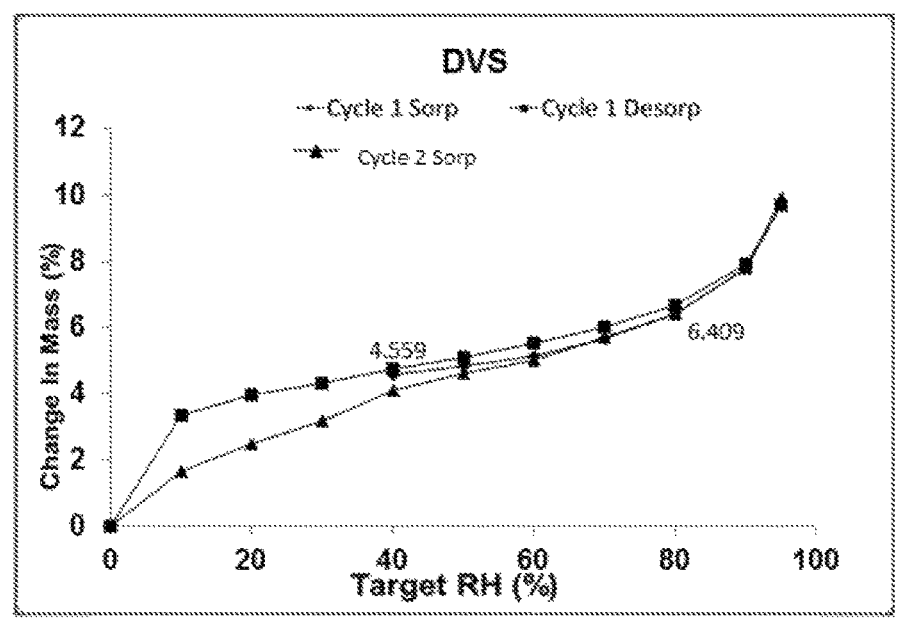
FIG. 10 shows a DVS plot of Form CS2 in example 4.
Figure 11:
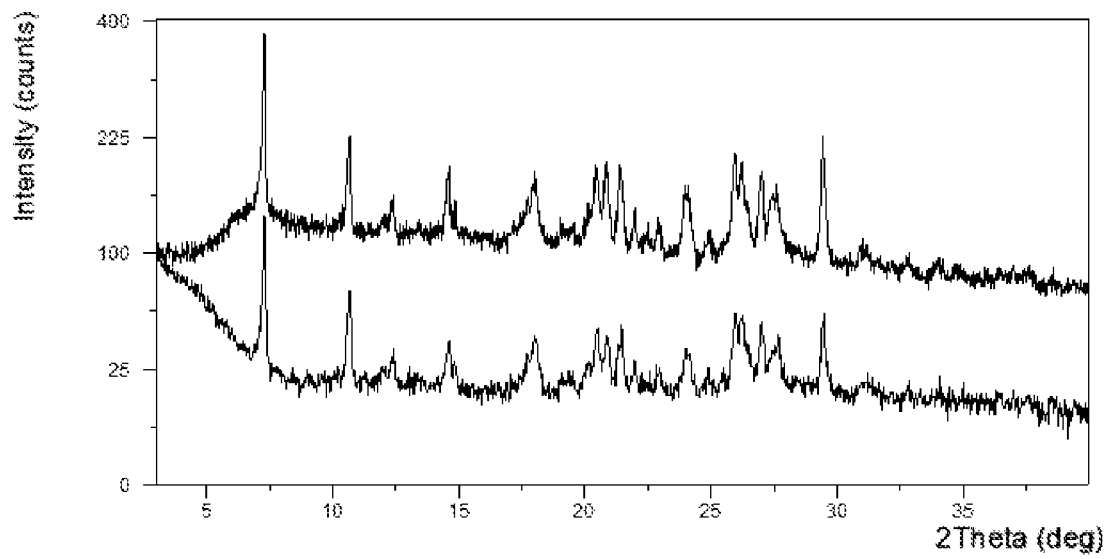
FIG. 11 shows an XRPD pattern overlay of Form CS2 before and after DVS test in example 4 (Top: XRPD pattern before DVS; Bottom: XRPD pattern after DVS).

6.2 mg of monohydrochloride Form CS2 was placed into dynamic vapor sorption (DVS) instrument, and then went through a 40%-95%-0-95% RH cycle at 25° C. The DVS plot was substantially as depicted in FIG. 10. The XRPD patterns overlay of solids before and after DVS test was substantially as depicted in FIG. 11 (Top: XRPD pattern before DVS; Bottom: XRPD pattern after DVS). No form change was observed for Form CS2 after DVS test.

Example 5 Hygroscopicity Test of Dihydrochloride Form CS3

Figure 12:
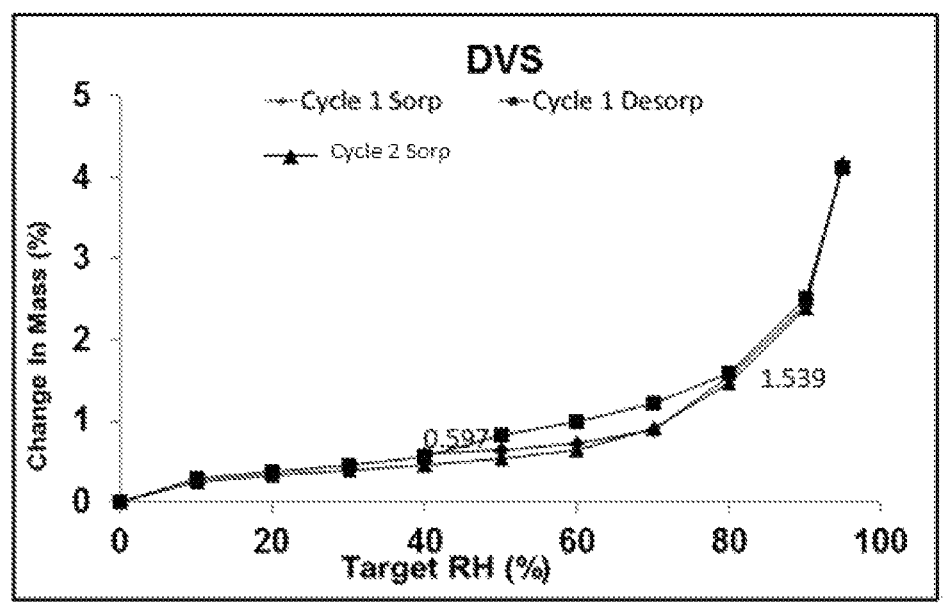
FIG. 12 shows a DVS plot of Form CS3 in example 5.
Figure 13:
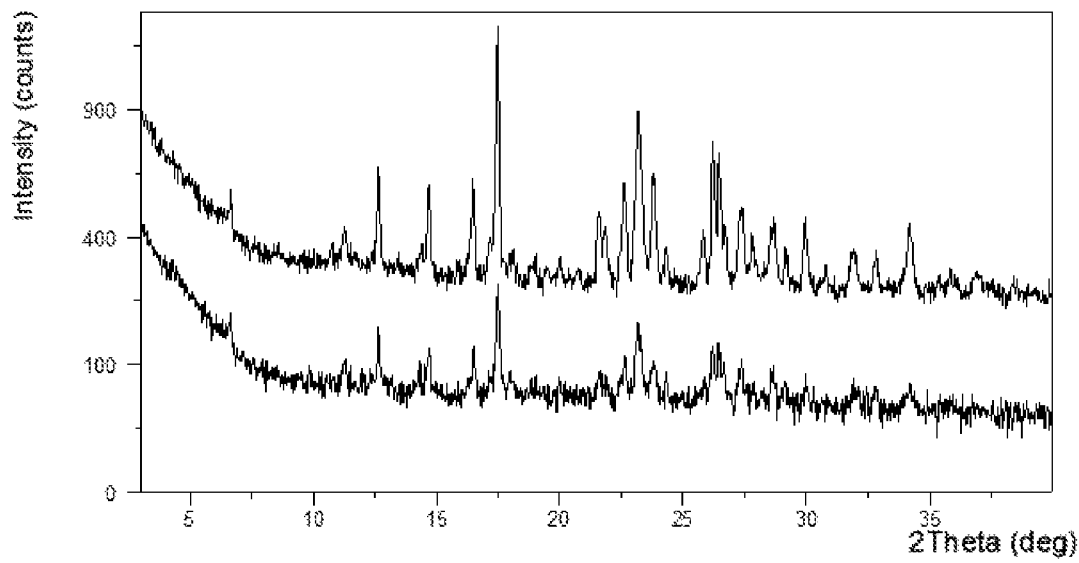
FIG. 13 shows an XRPD pattern overlay of Form CS3 before and after DVS test in example 5 (Top: XRPD pattern before DVS; Bottom: XRPD pattern after DVS).

7.9 mg of dihydrochloride Form CS3 was placed into dynamic vapor sorption (DVS) instrument, and then went through a 40%-95%-0-95% RH cycle at 25° C. The DVS plot was substantially as depicted in FIG. 12. The XRPD patterns overlay of solids before and after DVS test was substantially as depicted in FIG. 13 (Top: XRPD pattern before DVS; Bottom: XRPD pattern after DVS). No form change was observed for Form CS3 after DVS test.

Example 6 Stability Assessment of Monohydrochloride Form CS2

Figure 14:
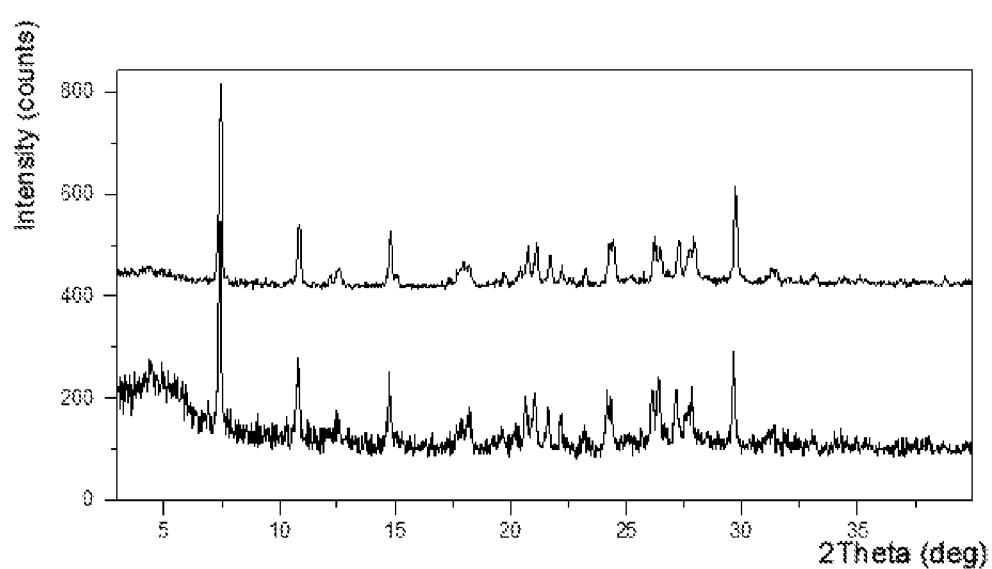
FIG. 14 shows an XRPD pattern overlay of Form CS2 before and after stored at 5° C. for 30 days in example 6 (Top: XRPD pattern before storage; Bottom: XRPD pattern after storage).

Form CS2 of the present disclosure was stored at 5° C. Samples were taken after 15 and 30 days to test XRPD and HPLC. The stability of From CS2 was mainly investigated. As summarized in Table 4, the results showed that Form CS2 has good stability. XRPD patterns overlay before and after storage for 30 days was substantially as depicted in FIG. 14.

TABLE 4

| | Solid Form | Purity |
|---|---|---|
| Initial | No form change | 99.53% |
| 15 days | No form change | 99.45% |
| 30 days | No form change | 99.44% |

Example 7 Stability Assessment of Dihydrochloride Form CS3

Figure 15:
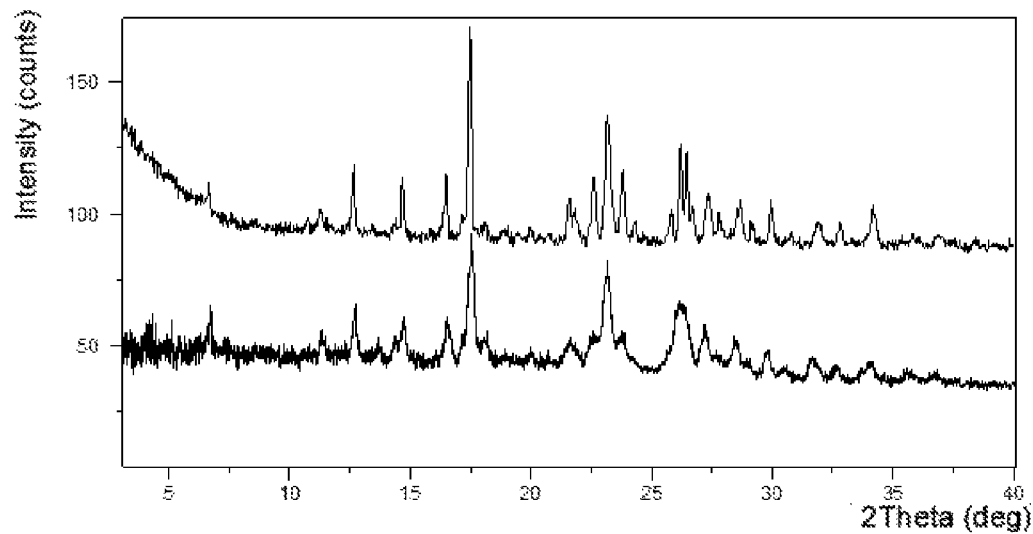
FIG. 15 shows an XRPD pattern overlay of Form CS3 before and after stored at 25° C./60% RH for 90 days in example 7 (Top: XRPD pattern before storage; Bottom: XRPD pattern after storage).

Form CS3 of the present disclosure was stored at 25° C./60% RH for 90 days. Samples were taken after 15, 30 and 90 days to investigate the stability of From CS3. As summarized in Table 5, the results showed that Form CS3 has good stability. XRPD patterns overlay before and after storage for 90 days was substantially as depicted in FIG. 15.

TABLE 5

| | Solid Form | Purity |
|---|---|---|
| Initial | No form change | 99.51% |
| 15 days | No form change | 99.60% |
| 30 days | No form change | 99.64% |
| 90 days | No form change | 99.50% |

Example 8 Dynamic Solubility Comparison of Form C of WO2016179415 and Form CS2

Form CS2 of the present disclosure and Form C of WO2016179415 were suspended into SGF (Simulated gastric fluids) and water to get saturated solutions. After equilibrated for 1 h and 4 h, concentrations of the saturated solutions were measured by HPLC. The results are listed in Table 6.

TABLE 6

| | Solubility | | | |
|---|---|---|---|---|
| | SGF | | $H_2O$ | |
| Time | Form CS2 (mg/mL) | Form C (mg/mL) | Form CS2 (mg/mL) | Form C (mg/mL) |
| 1 h | 1.13 | 0.49 | 2.17 | 0.08 |
| 4 h | 1.28 | 0.56 | 1.29 | 0.60 |

The results show that the solubility of Form CS2 in SGF and water is higher than that of Form C of WO2016179415.

Example 9 Particle Size Distribution of Form C of WO2016179415 and Form CS3

PSD was performed on Form CS3 of the present disclosure and Form C of WO2016179415. The results are summarized in Table 7.

TABLE 7

| | D(10)/μm | D(50)/μm | D(90)/μm |
|---|---|---|---|
| Form C | 2.35 | 18.26 | 118.8 |
| Form CS3 | 6.55 | 47.85 | 194.3 |

The results show that Form CS3 has larger particle size, which is favorable for isolation in production process.

Example 10 Mechanical Stability of Form C of WO2016179415, Form CS2 and Form CS3

Figure 16:
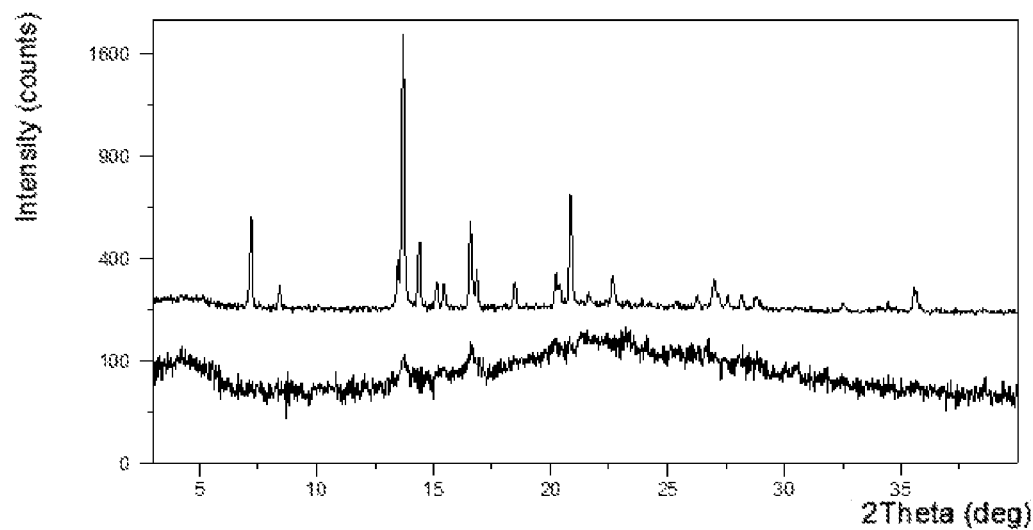
FIG. 16 shows an XRPD pattern overlay of Form C in WO2016179415 before and after grinding in example 10 (Top: XRPD pattern before grinding; Bottom: XRPD pattern after grinding).
Figure 17:
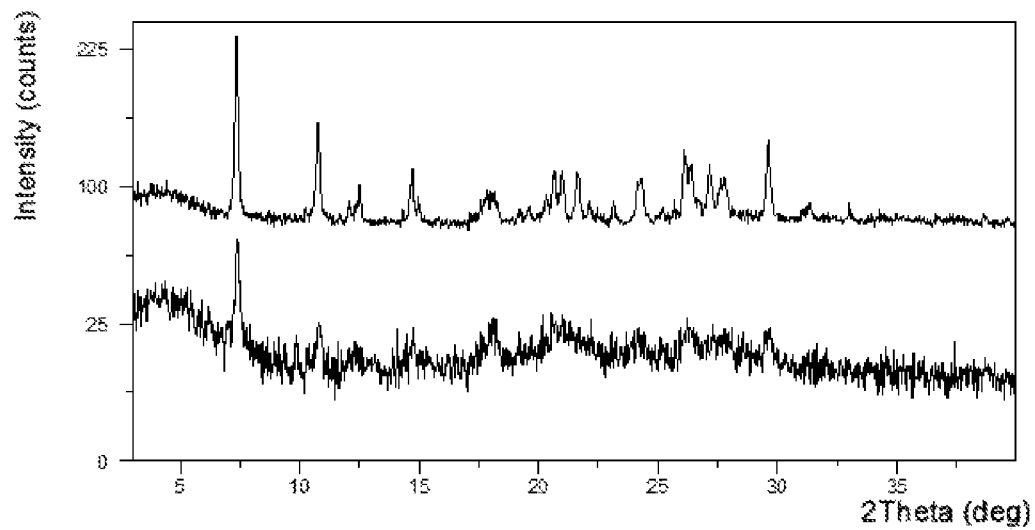
FIG. 17 shows an XRPD pattern overlay of Form CS2 before and after grinding in example 10 (Top: XRPD pattern before grinding; Bottom: XRPD pattern after grinding).
Figure 18:
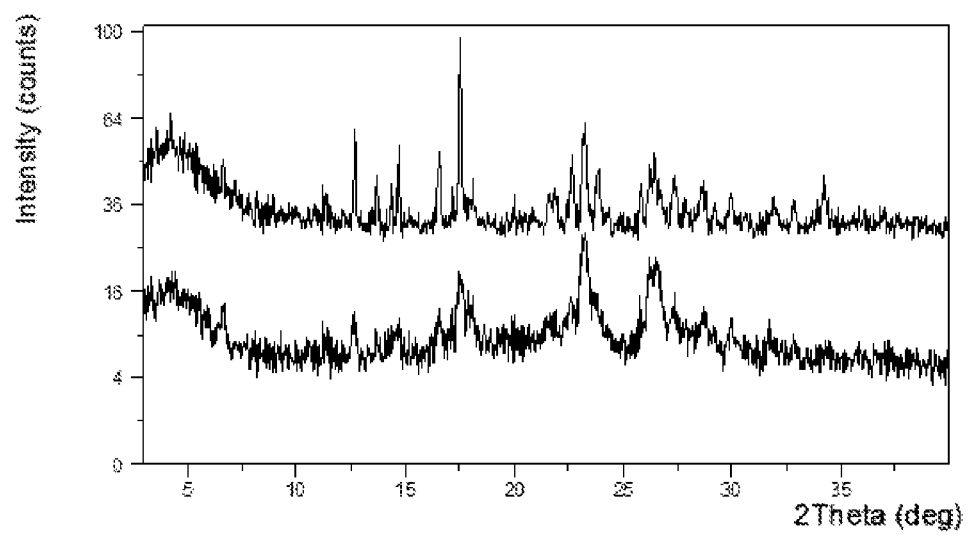
FIG. 18 shows an XRPD pattern overlay of Form CS3 before and after grinding in example 10 (Top: XRPD pattern before grinding; Bottom: XRPD pattern after grinding).

A certain amount of Form C of WO2016179415, Form CS2 and Form CS3 samples were placed in an agate mortar. After grinding for 5 minutes, the obtained solid was collected for XRPD characterization. The results of Form C of WO2016179415, Form CS2 and Form CS3 were substantially as depicted in FIG. 16, FIG. 17 and FIG. 18, respectively.

It can be seen from the figures that after grinding, the crystallinity of Form CS2 and Form CS3 decreased but the crystalline forms remained unchanged. Form C of WO2016179415 substantially changed to amorphous after grinding. Therefore, the mechanical stability of Form CS2 and Form CS3 is superior to that of Form C of WO2016179415.

It will be appreciated by those skilled in the art that certain modifications and variations can be made in the present invention. Such modifications and variations are also intended to be included within the scope of the appended claims.

The invention claimed is:

1. A crystalline form CS2 of PLX3397 monohydrochloride, wherein the X-ray powder diffraction pattern shows characteristic peaks at 2theta values of 7.2°±0.2°, 10.6°±0.2° and 29.3°±0.2° using CuKα radiation.

2. The crystalline form CS2 according to claim 1, wherein the X-ray powder diffraction pattern shows 1 or 2 characteristic peaks at 2theta values of 14.5°±0.2° and 21.4°±0.2° using CuKα radiation.

3. The crystalline form CS2 according to claim 1, wherein the X-ray powder diffraction pattern shows 1 or 2 characteristic peaks at 2theta values of 23.9°±0.2° and 26.9°±0.2° using CuKα radiation.

4. A process for preparing crystalline form CS2 of PLX3397 monohydrochloride of claim 1, wherein the process comprises: adding the solid of PLX3397 into a solvent of alkanes, adding dilute hydrochloric acid solution under stirring, reacting for 0.1-24 hours at 0-25° C., filtering and drying to obtain an off-white solid.

5. The process for preparing crystalline form CS2 according to claim 4, wherein said alkane is n-heptane, the molar ratio of HCl/PLX3397 is 1:1, said reaction temperature is 5° C., said reaction time is 0.5 hour, and the concentration of said dilute hydrochloric acid solution is 0.2-2 mol/L.

6. A method of treating tenosynovial giant cell tumor, comprising administering to a patient in need thereof a therapeutically effective amount of the crystalline form CS2 of PLX3397 monohydrochloride according to claim 1.

* * * * *